United States Patent
Miner et al.

(10) Patent No.: US 7,311,927 B2
(45) Date of Patent: Dec. 25, 2007

(54) ANTISEPTIC SOLUTIONS CONTAINING SILVER CHELATED WITH POLYPECTATE AND EDTA

(75) Inventors: Edwin Odell Miner, 4605 N. 650 E., Provo, UT (US) 84604; Craig Norman Eatough, Provo, UT (US)

(73) Assignee: Edwin Odell Miner, Provo, UT (US)

( * ) Notice: Subject to any disclaimer, the term of this patent is extended or adjusted under 35 U.S.C. 154(b) by 292 days.

(21) Appl. No.: 10/527,655

(22) PCT Filed: Sep. 25, 2003

(86) PCT No.: PCT/US03/30385

§ 371 (c)(1), (2), (4) Date: Mar. 14, 2005

(87) PCT Pub. No.: WO2004/028461

PCT Pub. Date: Apr. 8, 2004

(65) Prior Publication Data

US 2006/0240122 A1    Oct. 26, 2006

Related U.S. Application Data

(60) Provisional application No. 60/413,379, filed on Sep. 25, 2002.

(51) Int. Cl.
   *A61K 33/24*    (2006.01)
   *A61K 33/38*    (2006.01)
(52) U.S. Cl. ..................................... 424/617; 424/618
(58) Field of Classification Search ............... 424/617, 424/618
   See application file for complete search history.

(56) References Cited

U.S. PATENT DOCUMENTS 4,184,974 A * 1/1980 Van Leuven
4,267,168 A   5/1981 Van Leuven ................. 424/75
4,289,758 A   9/1981 Van Leuven ................ 424/132
6,344,218 B1 * 2/2002 Dodd et al.

* cited by examiner

*Primary Examiner*—Humera N Sheikh
(74) *Attorney, Agent, or Firm*—Kunzler & McKenzie

(57) ABSTRACT

A liquid antiseptic and cleanser having improved long-term stability includes at least the following principal ingredients: deionized water; silver ion, polypectate, and ethylenediaminetetraaceticacid (EDTA). Presently preferred embodiments of the technology also include glycerine; 1,2-propanediol (a.k.a. propylene glycol); at least one surfactant from any of the families of alkylsulfates, sulfonates, alkanolamides, betaines, amine oxides, sarcosinates and sulfosuccinates; and a buffering compound sufficient to achieve a pH value within a range of 7.2 to 7.8.

10 Claims, No Drawings

ANTISEPTIC SOLUTIONS CONTAINING SILVER CHELATED WITH POLYPECTATE AND EDTA

This application has a priority date based on Provisional Patent Application No. 60/413,379, which has a filing date of Sep. 25, 2002.

FIELD OF THE INVENTION

This invention relates to antiseptic formulations and, more particularly, to antiseptic formulations in which at least one metal compound serves as a biocidal agent.

BACKGROUND OF THE INVENTION

Professional journals of dentistry and medicine have documented the spread of infection that occurs in clinics, hospitals, patient rooms, public facilities and other noninstitutional settings when practitioners and staff fail to appropriately cleanse their hands. Given the often dire consequences of poor hygiene, practitioners must wash their hands with bewildering frequency. Alcohol, hydrogen peroxide, as well as iodine and chlorine containing compounds have long been recognized as effective antimicrobial and antiviral agents, thus their use in scrub and pre-surgical preparation is widely encouraged. However, recent studies have shown that repeated application of many of these compounds to the skin is physiologically damaging. In addition, when microbe populations are regularly subjected to specific antimicrobial chemical compounds, the microbes gradually evolve by developing chemical pumps which expel those compounds, thereby greatly reducing the effectiveness of the compound as an antimicrobial agent.

Certain metals have been shown to possess antiseptic qualities. Mercuric solutions, such as tincture of merthiolate and mercurachrome, were widely used in the twentieth century as antiseptics. However, studies showing that the use of such antiseptics resulted in the absorption of mercury through the skin, coupled with research indicating that the uptake of even small amounts of mercury resulted in the retardation of children, prompted their discontinuance. The search for alternative antiseptic compounds which do not damage the central nervous system, and which do not harm the skin and mucous membranes has been extensive.

Silver is a naturally-occurring metal that, when applied topically, has been shown to be lethal to a wide variety of disease-causing bacteria, fungi, molds, parasites, and viruses, yet relatively innocuous to the human body. Phoenician records from the period 700 to 100 B.C. indicate that silver vessels were used to keep vinegar, water and wine pure during long journeys and voyages. It is also known that early American settlers and pioneers used copper, gold and silver coins for medicinal and water purification purposes. The use of silver as a bactericide was documented as early as the late 1800s. In the past century, particularly the past two decades, silver has come to be widely recognized as an effective germicide and parasiticide. For such applications, silver has typically been used in the form of silver nitrate, silver oxide, or colloidal suspensions of silver compounds. For example, silver nitrate drops are routinely placed in the eyes of newborns in order to protect the eyes of infants— who might have become infected as they passed through the birth canal. Colloidal silver, either as elemental or silver oxide particulates, suspended in mineral oil or water bases, is being promoted for a wide variety of medicinal purposes via both internal ingestion and topical application. It is promoted as a treatment for mastitis and as a treatment for infections of the mucous membranes.

There is little indication that microbes have or can develop a resistance to silver, as it externally blocks respiration, rather than interfering with the internal metabolism of the organism.

In recent decades, extensive research has demonstrated that chelated silver is an active antimicrobial. The antimicrobial action reportedly occurs by blocking the respiration of microorganisms. Chelated silver is different from colloidal silver. Chelated means in solution, whereas colloidal means in suspension. In colloidal suspensions, minute silver particles are suspended or floating in an aqueous solution, and are not evenly dispersed throughout the liquid. Chelated solutions occur when a metal ion forms a heterocyclic ring with a bidentate ligand. Examples of bidentate ligands are carbonate and oxalate ions and ethylenediamine. As a general rule, five- or six-membered rings are favored. Because chelated silver ions are chemically bonded to nonmetallic ions, they are evenly dispersed throughout the solution. The even dispersal of chelated silver ions throughout the solution considerably enhances their antimicrobial action and effectiveness over time.

Three U.S. patents were issued to James W. Van Leuven covering a liquid antiseptic in which silver ions are chelated with sodium polypectate. U.S. Pat. No. 4,184,974 to Van Leuven discloses a liquid cleaner, lubricant and topical biocidal agent containing lauryl diethanolamide, propylene glycol, glycerine, sodium polypectate, a water soluble detergent, silver ions, and sufficient base to maintain pH within a range of 7.2 to 7.8, and distilled water. U.S. Pat. No. 4,267,168, which is a continuation of the application which issued as the '974 patent, discloses a method for treating external human tissue with the liquid cleaner, lubricant and topical biocidal agent disclosed in U.S. Pat. No. 4,184,974. U.S. Pat. No. 4,289,758, which is a continuation of the application which issued as the '168 patent, discloses a liquid biocidal agent containing about 100 to 400 parts per million sodium polypectate, about 13 to 250 parts per million silver ion, about 4 to 8% glycerine, sufficient base to maintain a pH in the range of from about 7.2 to 7.8, and distilled water.

A known drawback to the solutions patented by Van Leuven is that chelation of the silver ions lacks long-term stability. The instability is apparently due either to a gradual decomposition of the polypectate molecules or the gradual formation of extraneous compounds which have a greater affinity for the silver ions than to the polypectate molecules. The decomposition is accelerated in the presence of extreme cold or heat and light. The greater the heat or the greater the energy of the incident light, the more rapid the decomposition.

SUMMARY OF THE INVENTION

A liquid antiseptic and cleanser having improved long-term stability includes at least the following principal ingredients: deionized water; silver ion, sodium polypectate, and ethylenediaminetetraaceticacid (EDTA). Enhanced long-term stability and extended antimicrobial effectiveness of the solution is provided by strengthening the chelation bonding of the sliver ions. Presently preferred embodiments of the cleanser also include glycerine, 1,2-propanediol (a.k.a. propylene glycol), and at least one surfactant from any of the families of alkylsulfates, sulfonates, alkanolamides, betaines, amine oxides, sarcosinates and sulfosuccinates. A preferred embodiment of the technology that has been actually formulated and marketed includes the following ingredients by weight: about 70-80% deionized water, 2.5-5.5% TEA dodecylbenzene sulfonate; 1.5-3.25% lauramide DEA; 5.5-11.5% glycerine; 3.0-5.5% propanediol; 0.005-0.015% sodium polypectate and 0.005-0.015% EDTA; 0.01-0.03% silver ion; and a buffering compound sufficient to achieve a pH value within a range of 7.2 to 7.8

DETAILED DESCRIPTION OF THE INVENTION

A liquid antiseptic and cleanser having improved long-term stability includes at least the following principal ingredients: deionized water; silver ion, polypectate, and ethylenediaminetetraaceticacid (EDTA). The addition of EDTA to the formulation improves the strength of the chelation bonds, and thereby enhances its long-term stability.

Presently preferred embodiments of the technology also include glycerine, 1,2-propanediol (a.k.a. propylene glycol), and at least one surfactant from any of the families of alkylsulfates, sulfonates, alkanolamides, betaines, amine oxides, sarcosinates and sulfosuccinates. A preferred embodiment of the technolgy that has been actually formulated and marketed includes the following ingredients by weight: about 70-80% deionized water, 2.5-5.5% TEA dodecylbenzene sulfonate; 1.5-3.25% lauramide DEA; 5.5-11.5% glycerine; 3.0-5.5% propanediol; 0.005-0.015% sodium polypectate and 0.005-0.015% EDTA; 0.01-0.03% silver ion; and a buffering compound sufficient to achieve a pH value within a range of 7.2 to 7.8. At a pH less than 7.0, the polypectate can gel. A number of buffering compounds of the strong base-weak acid type can be used in the compositions so long as they are compatible with the other materials that are present. As ammonium hydroxide is quite compatible for use with the combination of sodium polypectate, EDTA, and silver nitrate, it can be used as the buffering compound and will comprise about 0.03% of the total composition.

Sodium polypectate may be obtained commercially or can be prepared by treating pectin with sodium carbonate in order to solubilize it. The polypectate chelates readily with the alkaline earth ions such as calcium and magnesium. The acidic form of polypectate is known as polygaluctronic acid. The chelation may be performed using the latter substance and not the sodium salt thereof. In the claims which follow, polygaluctronic acid should be considered interchangeable with polypectate.

In order to provide an aqueous environment that is conducive to the formation of chelated complexes between silver ion and EDTA or polypectate, a solution containing silver nitrate and ammonia (in the form of amonium hydroxide) is first formulated, after which EDTA and/or polypectate are introduced into the solution. A number of complex ions and neutral molecules are known to coexist in a state of equilibrium within the mixture of silver nitrate and ammonia. As both EDTA and polypectate have a greater affinity for the silver ions than do the ammonium and hydroxide ions, the formation of chelated complexes with the former two compounds is facilitated by the prior addition of ammonia to the silver nitrate. The following stoichiometry is typical of the formulations employed during the chelation process. Parts A and B are prepared separately, then mixed together to form the chelated silver solution. Alternatively, parts A and B may be added to a detergent solution.

Part A

| | |
|---|---|
| silver nitrate | 30-60 grams |
| deionized water | 2 liters |
| ammonium hydroxide (reagent grade) | 200 ml |

Part B

| ethylenediaminetetraaceticacid (EDTA) | |
|---|---|
| sodium polypectate | 19.5 grams |
| glycerine | 200 mililiters |
| deionized water | 5 liters |

A Material Safety Data Sheet prepared by LaSal Laboratories of Provo, Utah indicates that a chelated silver formulation prepared in accordance with the present invention, according to the OSHA Hazard Communications Standard, 29 CFR 1910.1200, contains no hazardous ingredients. It was also determined that, from the standpoint of ingestion, the formulation was practically non toxic, with the acute oral LD50 level in rats being approximately 5 gram per kilogram of body weight. It was also ascertained that the formulation was not a primary skin irritant, and that it was only slightly to moderately irritating to the eyes of small animals.

Although the silver formulations of the present invention may be considered generally harmless to vertebrate animals, they possess remarkable antimicrobial qualities. Tests have also been performed by LaSal Laboratories in order to study the antibacterial effectiveness of the chelated silver formulations of the present invention. One representative test, performed on Aug. 20, 2003, used the following methodology to ascertain the effectiveness of a chelated silver solution, prepared in accordance with the present invention, against a common infectious bacterial agent.

1. Test Organisms.
    The test suspension was prepared by growing a five ml culture of *Staphylococcus aureus* ATCC #6538 in Todd Hewitt broth in a 50 ml conical polypropylene centrifuge tube at 37° C., and shaking at 250 RPM for 20 hours. The culture was pelleted by centrifugation, washed with five ml of sterile 18MΩ water, centrifuged again, and resuspended in a final volume of one ml of sterile water.

2. Neutralizer.
    A neutralizer solution was formulated with the following composition: Tween 80—10.0%, Lecithin—1.7%, Tryptone—1.0%, Sodium thiosulfate—0.6%, Yeast extract—0.5%, NaCl—0.5%, Cysteine—0.04%, and Tamol—6.0%. This solution was sterilized by autoclaving.

3. Suspension Test Procedure.
    3.1 A 9.9 ml aliquot of the chelated silver solution was placed in a sterile 20 mm×150 mm tube. The tube was equilibrated in a 20° C. water bath.
    3.2 The tube was inoculated with 100 µl of the test organism suspension at time zero. The tube was mixed vigorously to obtain a uniform suspension.
    3.3 After exactly three minutes, one ml of organism/chelated silver solution was removed to nine ml of neutralizer. Two minutes later, the neutralized suspension was serially diluted 1:10, in physiological saline solution (PSS).

3.4 The number of viable organisms in each dilution tube was assayed by membrane filtration. One ml aliquots were plated in duplicate from selected dilution tubes. The membranes were washed with about 100 nml of sterile PSS and removed to Trypticase Soy Agar plates. The plates were incubated at 37° C. for 21 hours.

3.5 The number of colonies on each filter was counted and the log reductions and percent kill values were computed.

4. Controls.

4.1 A titer of the test suspension was performed by membrane filtration of selected 1:10 dilutions in PSS of the test organism suspension.

4.2 A neutralization control was performed by adding one ml of disinfectant to nine ml of neutralizer and inoculating this tube with 100 μl of the 1:1×10$^4$ dilution of the test suspension. This tube was allowed to sit for about 20 minutes, then diluted 1:10 and 1:100. One ml aliquots from these three tubes were assayed in duplicate by membrane filtration.

4.3 Sterility controls for each solution used in the test were performed by filtering 1 ml samples in duplicate. A 100 ml aliquot was filtered for the PSS control.

5. Results 5.1 Titer.

| Dilution: | $10^{-7}$ | $10^{-8}$ | $10^{-9}$ |
|---|---|---|---|
| Number of colony forming units (CFU): | TNC | 96 | 6 |
| | TNC | 96 | 9 |

(TNC = total not counted)

5.2 Suspension Tests.

| Dilution of *Staphylococcus*/chelated silver solution suspension: | $10^{-1}$ | $10^{-2}$ | $10^{-3}$ |
|---|---|---|---|
| CFU for each plate after 3 minutes: | 108 | 15 | 0 |
| | 117 | 9 | 0 |

5.3 Neutralizer Control

| CFU for each plate after 3 minutes: | undiluted | $10^{-1}$ | $10^{-2}$ |
|---|---|---|---|
| | TNC | TNC | 128 |
| | TNC | TNC | 112 |

5.4 Sterility controls

Duplicate assays on each solution produced the following CFU counts:

| PSS | Water | Neutralizer | Chelated Silver solution |
|---|---|---|---|
| 0 | 0 | 0 | 0 |
| 0 | 0 | 0 | 0 |

6. Conclusion

Results of the titer showed a viable *staphylococcus* concentration of 9.60×10$^9$ organisms per ml in the original suspension. Inoculation of the 9.9 ml of chelated silver solution with this suspension produced an initial concentration of 9.60×10$^7$ organisms per ml in the assay tube.

Results from these procedures allowed log reduction (LR) and percent kill (PK) values to be calculated using the formulas:

$LR=-Log(S/So)$, where S=concentration of viable organisms after three minutes; and So=the initial concentration of viable organisms at time zero.

$PK=(1-(S/So))\times100$.

Using these formulas, an LR value of 4.93 and a PK value of 99.9988 were calculated. In summary, the chelated silver solution produced almost a five-log reduction of *S. aureus* within three minutes. This is equal to or greater than the antimicrobial activity of most other topical antiseptic solutions currently in use.

Although the invention has been disclosed as a formulation having particular ingredients, each present within a specific range of concentration, it will be obvious to those having ordinary skill in the art that changes and modifications may be made thereto without departing from the scope and the spirit of the invention as hereinafter claimed.

What is claimed is:

1. A liquid antiseptic and cleanser having enhanced long-term stability comprising:
   about 70-80% water by weight;
   at least one surfactant compound constituting about 4.0-8.75% by weight;
   about 5.5-11.5% glycerine by weight;
   about 3.0-5.5% 1,2-propanediol by weight;
   about 0.005-0.015% sodium polypectate;
   and about 0.005-0.015% EDTA;
   about 0.01-0.03% chelated silver ion; and
   sufficient base to achieve a pH value within a range of 7.2 to 7.8.

2. The liquid antiseptic and cleanser of claim 1, wherein said at least one surfactant is selected from the group consisting of alkylsulfates, sulfonates, alkanolamides, betaines, amine oxides, sarcosinates and sulfosuccinates.

3. The liquid antiseptic and cleanser of claim 1, wherein said at least one surfactant comprises:
   about 2.5-5.5% TEA dodecylbenzene sulfonate, by weight; and
   about 1.5-3.25% lauramide DEA, by weight.

4. A method of preparing a liquid antiseptic, comprising the steps of:
   combining water silver ion and aqueous ammonia to form a silver ammonium complex solution;
   combining ethylenediaminetetraaceticacid (EDTA), sodium polypectate, glycerine and water to form a chelating solution;
   combining the silver ammonium complex solution with the chelating solution to form a chelated silver solution comprising about 0.01-0.03% chelated silver ion, about 0.005-0.015% EDTA, about 0.005-0.015% sodium polypectate, and about 5.5-11.5% glycerine.

5. The method of claim 4, which further comprises the step of adding at least one surfactant compound to the chelated silver solution.

6. The method of claim 4, which further comprises the step of adding 1,2-propanediol to the chelated silver solution.

7. The method of claim 4, which further comprises the step of adding least one surfactant to the chelated silver solution, said at least one surfactant being selected from the group consisting of alkylsulfates, sulfonates, alkanolamides, betaines, amine oxides, sarcosinates and sulfosuccinates.

8. The method of claim 4, which further comprises the step of adding at least the surfactants TEA dodecylbenzene sulfonate and lauramide DEA to the chelated silver solution.

9. The method of claim 4, which further comprises the step of adding a buffering compound to the chelated silver solution in an amount sufficient to adjust the pH value of the chelated silver solution to between about 7.2 and 7.8.

10. The method of claim 4, which further comprises the step of adding ammonium hydroxide to the chelated silver solution in an amount to adjust the pH value of the chelated silver solution to between about 7.2 and 7.8.

* * * * *

UNITED STATES PATENT AND TRADEMARK OFFICE
CERTIFICATE OF CORRECTION

PATENT NO. : 7,311,927 B2  Page 1 of 1
APPLICATION NO. : 10/527655
DATED : December 25, 2007
INVENTOR(S) : Edwin Odell Miner et al.

It is certified that error appears in the above-identified patent and that said Letters Patent is hereby corrected as shown below:

Column 2, Line 62
 "the sliver ions" ---should read --the silver ions--

Column 3, Line 54
 "form of amonium" ---should read --form of ammonium--

Column 5, Line 4
 "100 nml of sterile PSS" ---should read --100 mml of sterile PSS--

Column 7, Line 2
 "step of adding least" ---should read --step of adding at least--

Signed and Sealed this

Thirteenth Day of May, 2008

JON W. DUDAS
*Director of the United States Patent and Trademark Office*